US005957933A

United States Patent [19]
Yanof et al.

[11] Patent Number: 5,957,933
[45] Date of Patent: Sep. 28, 1999

[54] INTERCHANGEABLE GUIDANCE DEVICES FOR C.T. ASSISTED SURGERY AND METHOD OF USING SAME

[75] Inventors: Jeffrey H. Yanof, Solon; Laura L. Goldstein, Parma; Fred C. Jensen, Chagrin Falls; James C. Foster, Independence; Christopher Bauer, Westlake, all of Ohio

[73] Assignee: Picker International, Inc., Highland Heights, Ohio

[21] Appl. No.: 08/980,253

[22] Filed: Nov. 28, 1997

[51] Int. Cl.[6] .......... A61B 19/00

[52] U.S. Cl. .......... 606/130; 606/129

[58] Field of Search .......... 606/129, 130, 606/1, 205; 378/901

[56] References Cited

U.S. PATENT DOCUMENTS

| | | | |
|---|---|---|---|
| 4,583,538 | 4/1986 | Onik et al. | 128/303 |
| 4,651,732 | 3/1987 | Frederick | 128/303 |
| 4,733,661 | 3/1988 | Palestrant | 128/303 |
| 5,318,589 | 6/1994 | Litchman | 606/205 |
| 5,494,034 | 2/1996 | Schlondorff et al. | 606/130 |
| 5,575,798 | 11/1996 | Koutrouvelis | 606/130 |
| 5,628,327 | 5/1997 | Unger et al. | 128/749 |
| 5,792,247 | 8/1998 | Evans et al. | 606/130 |

*Primary Examiner*—Michael Buiz
*Assistant Examiner*—Vy Q. Bui
*Attorney, Agent, or Firm*—Fay, Sharpe, Beall, Fagan, Minnich & McKee, LLP

[57] ABSTRACT

A stereotactic guide apparatus 100 is provided for use with a CT scanner device 18 for guiding the entry of a probe into a patient's body. The CT scanner device is provided with a stereotactic arm member 30 having a first base end 42 connected to the CT scanner device 18 and a second free end 40 movable relative to the CT scanner device. The stereotactic surgical instrument guide apparatus includes a first end effector member 106 including a guide channel 152 defining a probe insertion path 150. The surgical instrument guidance device further includes a second end effector member 104 on the free end of the stereotactic arm member and including a laser light source 108 generating a light guide beam along the probe insertion path 150. Each of the first and second end effector members are selectively releasably attached to the free end of the stereotactic arm member and, further, are adapted to provide respective first and second device identification signals to the CT scanner device through the stereotactic arm member. The top end effector member 104 is preferably stationary in use during interventional procedures and the bottom end effector member 106 is selectively retractable into a hollow support tube 142. Alternatively, the first and second end effector members are selectively pivotally attached to the free end of the stereotactic arm member.

20 Claims, 9 Drawing Sheets

INTERCHANGEABLE GUIDANCE DEVICES FOR C.T. ASSISTED SURGERY AND METHOD OF USING SAME

BACKGROUND OF THE INVENTION

The present invention relates to the medical diagnostic imaging and minimally invasive stereotactic surgery arts. It finds particular application in conjunction with an integrated CT scanner and mechanical arm guided minimally invasive surgical tools and will be described with particular reference thereto. It is to be appreciated, however, that the invention is also applicable to guiding interventional surgical tools in conjunction with magnetic resonance imaging and other imaging systems capable of generating volumetric images. The system is also applicable to other surgical tools used in conjunction with real time imaging systems capable of monitoring a region of the patient during a minimally invasive surgical procedure.

Heretofore, several surgical instrument guidance devices have been proposed for use in conjunction with a CT scanner to allow a user to accurately place a catheter, drainage tube, or biopsy probe within a patient's body. U.S. Pat. No. 4,733,661 describes a hand held guidance device including a planar base with a bubble level to maintain the base in a horizontal position. Needle guides are provided on a support arm pivotally secured to the base, the guides slidingly supporting a catheter at a desired angle as the catheter into the patient's body. The guidance device includes a reference line formed upon the base adapted to be aligned with a transverse light beam projected by the CT scanner apparatus. Although it may be possible for the device to be used to accurately insert a biopsy needle within a patient's body without damage to any unintended targets, one major disadvantage of the device is its reliance upon an accurate human alignment between the reference line defined on the base of the device and the transverse light beam projected by the CT scanner. It would, therefore, be desirable to provide a surgical instrument guidance device which is not dependent upon a manual alignment step.

U.S. Pat. No. 4,583,538 proposes a free standing biopsy guide that is adapted to hold needles or probes at various selectable calculated angles. In using the device proposed in that patent, a reference point on the patient's body is found that exactly correlates to a point on the CT scan. This is accomplished by means of a localization device placed on the patient's skin which can be identified in cross section on the CT scan. Measurements of the localization device on the CT scan are then correlated to the device on the patient. The free standing biopsy guide is then adjusted according to those calculations. One disadvantage of the device taught by this patent is the time required to correlate the patient body reference point with selected points on the CT scan. In addition, certain inaccuracies may be introduced during the point correlation step and while adjusting the free standing guidance device. Accordingly, it would be desirable to provide a biopsy or other surgical instrument guide that is rigidly affixed to the CT scanner apparatus whereby precise and automatic correlation between the coordinate systems of the guidance device, patient table, and patient image volume are automatically established.

U.S. Pat. Nos. 5,628,327 and 4,651,732 propose various devices for supporting a laser apparatus for use in laser guided biopsies or other interventional procedures. However, neither of these apparatus provide for a combined laser and cannula guidance system. Further, neither of these teachings suggest an interchangeable surgical instrument guidance device.

The present invention provides a new and improved interchangeable surgical instrument guidance device and method for using same which overcomes the above-referenced problems and others.

SUMMARY OF THE INVENTION

In accordance with one aspect of the present invention, an interchangeable surgical instrument guidance device is provided. The guidance device is used with a stereotactic arm member having a base end rigidly connected to a CT scanner device and a second free end movable relative to the CT scanner device for guiding the entry of a probe into a patient's body. The guidance device includes a first and second end effector member disposed on the free end of the stereotactic arm. The first end effector member carries a guide channel defining a probe insertion path. The second end effector includes a light source generating a light guide beam along the probe insertion path. The light guide beam together with the guide channel facilitate simultaneous mechanical and laser guided interventional procedures.

In accordance with another aspect of the present invention, the first and second end effector members are selectively releasably attached to the free end of the stereotactic arm member.

Still further in accordance with the present invention, the end effectors are interchangeable and may include such tools as orthopedic drill attachments, ultrasound probes, and the like.

Still further, yet another aspect of the present invention, each of the first and second end effector members forming the surgical instrument guidance device are selectively pivotally attached to the free end of the stereotactic arm member.

According to still yet another aspect of the present invention, the guide channel disposed on the bottom end effector member of the guidance device is retractable relative to the probe insertion path to facilitate the entry of the probe into the patient's body.

In accordance with another aspect of the present invention, the guide channel provided on the bottom end effector member is retractable relative to the probe insertion path following a substantially arcuate path.

Still other advantages and benefits of the invention will become apparent to those skilled in the art upon a reading and understanding of the following detailed description.

BRIEF DESCRIPTION OF THE DRAWINGS

The invention may take physical form in certain parts and arrangements of parts, a preferred embodiment of which will be described in detail in this specification and illustrated in the accompanying drawings which form a part hereof, and wherein.

DETAILED DESCRIPTION OF THE PREFERRED EMBODIMENT

Figure 1:
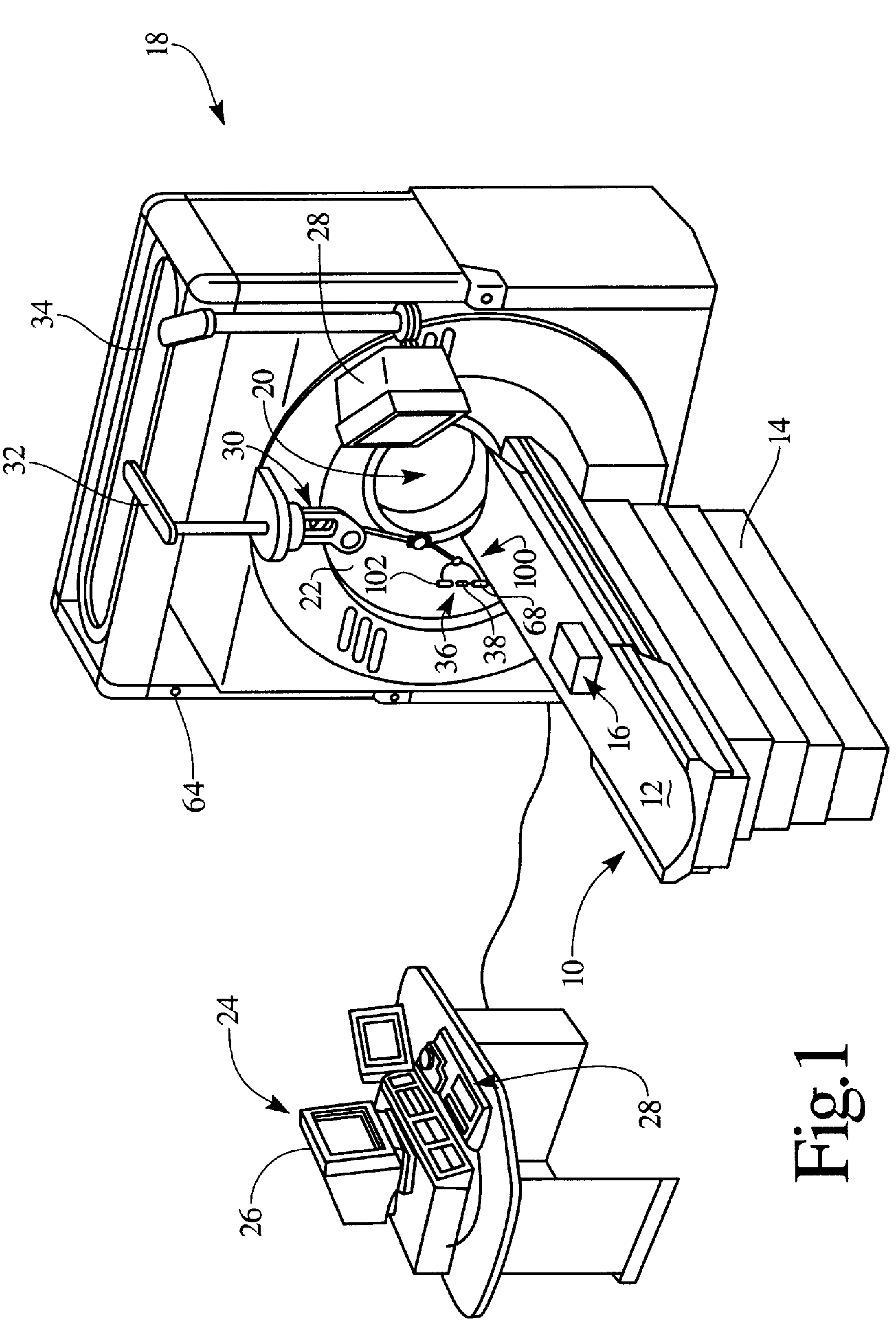
FIG. 1 is a diagrammatic illustration of a CT scanner and interchangeable surgical instrument guidance device in accordance with the present invention.

Referring now to the drawings wherein the showings are for the purposes of illustrating the preferred embodiments of the invention only and not for purposes of limiting same, with reference first to FIG. 1, a patient table or support 10 includes a patient supporting surface 12 that is mounted for longitudinal movement relative to a base portion 14. The base portion 14 includes a motor for raising and lowering the patient support surface 12 and for moving the patient support surface longitudinally. Position encoders are also provided for generating electrical signals indicative of the height and longitudinal position of the patient support. The patient support includes a calibration marker 16 disposed at a known, fixed location.

A planning, preferably volumetric diagnostic imaging apparatus 18 is disposed in axial alignment with the patient table such that a patient or subject on the patient support surface 12 can be moved into and through a bore 20 of the volumetric imager. In the illustrated embodiment, the volumetric imager is a CT scanner which includes an X-ray tube mounted for repeated circular travel within a preselected plane. The X-ray tube projects a fan-shaped beam of radiation through a ring 22 of radiation translucent material, through the patient support 12, through a region of interest of the subject, and to a ring or arc of radiation detectors positioned opposite the X-ray tube. As the X-ray tube rotates within the plane, a series of data lines are generated, which data lines are reconstructed into at least a slice image by a reconstruction processor included in a control console 26. The control console is typically remotely located in a shielded room adjacent the scan room containing the imaging apparatus 18. More specifically to the preferred embodiment, the patient support 12 moves longitudinally as the X-ray tube is rotating around the subject such that a selected volume of the patient is scanned along a spiral path or a series of slices. The position of the X-ray tube is monitored by a rotational position encoder, and the longitudinal position of the patient support is monitored by a longitudinal position encoder within the table 10. The reconstruction processor reconstructs a volumetric image representation from the generated data lines. The control console 24 typically includes one or more monitors 26 and various standard operator input devices, such as a keyboard, trackball, mouse, or the like. An interventionist control console 28 is supported from overhead on a track atop the CT scanner as shown.

A mechanical arm assembly 30 is supported from overhead by a support carriage 32 movable on an oval track system 34 affixed to the top of the volumetric diagnostic imaging apparatus 20 as generally shown. The support carriage is preferably lockable in one or more predetermined fixed locations on the oval track so that a minimally invasive surgical instrument 36 carried on an interchangeable surgical instrument guidance device 100 formed in accordance with the present invention can be positioned in monitored positions and orientations by an interventionist in preparation for and in carrying out a surgical procedure. The surgical instrument illustrated in the FIGURE includes a laser guided biopsy needle 38 carried by a combined laser and cannula guidance device 102 formed in accordance with a first preferred embodiment of the present invention which will be described below. Overall, however, the position and orientation of the guidance device and the surgical instrument carried thereon are determined by the position of the mechanical arm assembly 30 and the location of the support carriage 32 on the oval track system 34.

Figure 2:
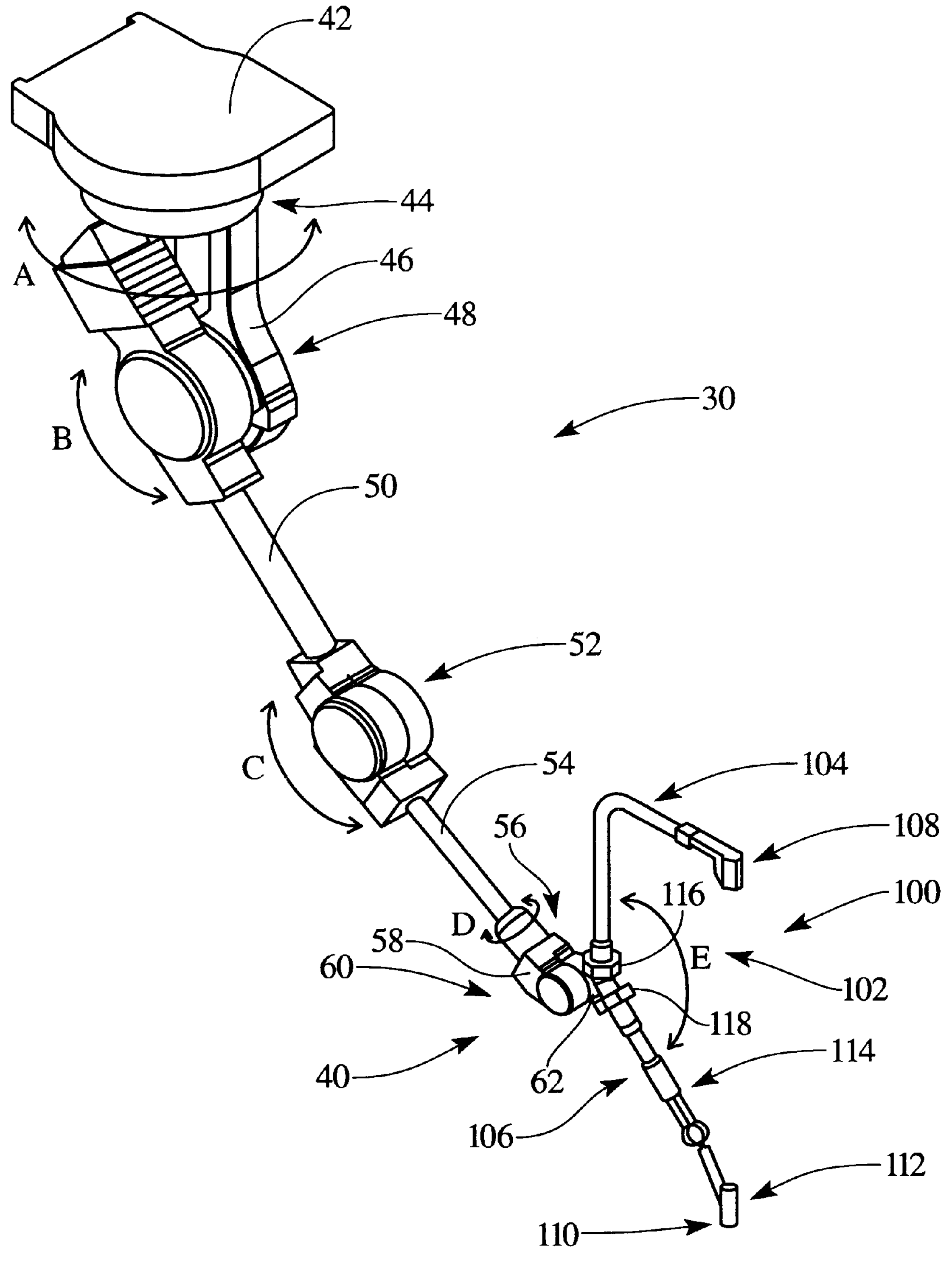
FIG. 2 is a perspective view of a mechanical arm assembly carrying a guidance device formed in accordance with the present invention.

The frameless stereotactic mechanical arm assembly 30 is shown generally in FIG. 2 and includes a plurality of arm segments which are interconnected by pivot members forming joints between the arm segments. In that way, a free end 40 of the arm is selectively movable in multiple orientations as necessary to position the surgical instrument 36 into various desired positions over the patient support 12. A base member 42 is rigidly connected to the gantry 32 using suitable fasteners, epoxies, or the like. A base joint 44 permits rotation of a primary support carriage 46 in a direction marked A. Similarly, from the immovable base end of the arm, a shoulder joint 48 permits rotation of an upper arm member 50 in a direction marked B, an elbow joint 52 permits rotation of a lower arm member 54 in a direction marked C, a forearm joint 56 permits rotation of a knuckle member 58 in a direction marked D, and, lastly, a wrist joint 60 permits rotation of a wrist member 62 in a direction marked E.

In order to determine the position and orientation of the wrist member 62 with respect to the imaging apparatus reference frame and the volumetric image representation obtained by the imaging apparatus, at least one position resolver (not shown), preferably an optical incremental encoder, is provided at each joint of the mechanical arm assembly 30 to monitor increment articulation and rotation of the arm segments relative to each other. The optical incremental encoders generate feedback pulses indicative of the movement and relative position of the various arm members in a well known manner. The feedback pulses are carried back to an imaging apparatus control circuit using suitable wires or flexible shielded cables extending through the multiple members of the arm assembly.

In addition to the above, according to the present invention, in order to determine the position and orientation of the surgical instruments relative to the imaging apparatus reference frame and the volumetric image representation obtained by the imaging apparatus, each interchangeable surgical instrument guidance device 100 is adapted to provide a unique identification signal. The signal is used by the imaging apparatus control circuit to index a look up table for retrieving various physical dimensional and other functional parameters corresponding to the one or more guidance devices connected to the wrist member 62. In this manner, the physical dimension and other functional parameters, together with the mechanical interconnection which is measured by the resolvers and encoders, provides an accurate indication of the position and orientation of the guidance device 100 relative to the CT scanner and, hence, relative to the image acquired by the CT scanner.

An imaging apparatus home position docking port 64 is provided on a forward side of the base member 42 of the stereotactic arm assembly 30. In the orientation shown in the FIGURE, the support carriage 32 and the arm assembly carried thereon is accurately positioned in a known predetermined relationship with respect to the calibration marker area 16 on the patient supporting surface 12 of the imaging apparatus 18. Preferably, the mathematical relationship between the calibration marker area 16 and the home position docking port 64 is permanently established during a calibration procedure using a calibration phantom typically performed by a service technician during initial installation of the imaging apparatus. A specialized arm docking connection member (not shown) is adapted to connect the mechanical arm assembly to the home position docking port 64 between each interventional procedure. Appropriate software within the imaging apparatus ensures that new interventional procedures are not initiated until the arm is returned to the home position docking port 64. As an extra precautionary measure to verify the relative orientation and position of the guidance device 100 relative to the patient support, a tip of the surgical instrument or pointer may be touched to the calibration marker area 16 and an assessment made whether the electronic signal is indicative of patient support location and surgical instrument location, in fact, placing both at the same point in space.

Other mechanisms for monitoring the guidance device 100 type and the position of the mechanical arm assembly 30 are also contemplated. For example, a plurality of first transmitters, such as light emitting diodes, are mounted in a fixed, known relationship to the mechanical arm assembly 30. A plurality of second transmitters, such as light emitting diodes, are mounted to the guidance device 100. The plurality of second transmitters includes at least one transmitter adapted to generate an identification signal unique to each guidance device. An array of receivers is mounted in a fixed relationship to the CT scanner, preferably affixed to the ceiling of the room. Each time a different type of guidance device 100 is attached to the mechanical arm assembly 30, the diode emitters are actuated and the emitted signals received by the receivers. The guidance device type and the position and orientation of the mechanical arm assembly and the guidance device on the arm are accurately and quickly calculated by decoding the identification signal and using geometric triangulation techniques for the position signals. By positioning the guidance device on a plurality of markers, preferably three or more, e.g., the several markers in the calibration marker area 16 which are mounted in a fixed, known relationship to the coordinate system of the CT scanner, the guidance device coordinate system, and hence the surgical instrument coordinate system can be readily correlated with the CT scanner coordinate system and the coordinate system of the patient table.

Figure 3:
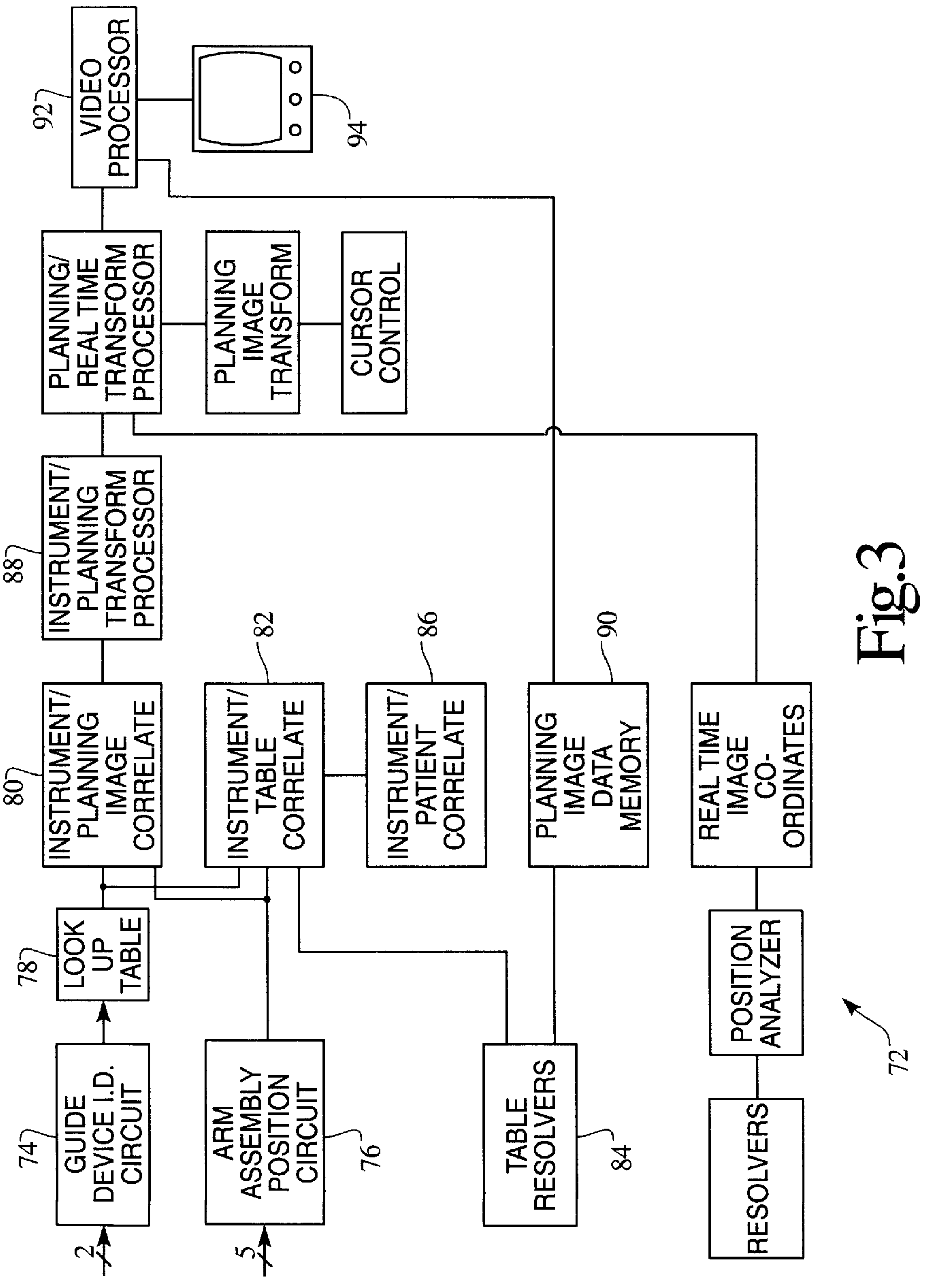
FIG. 3 is a diagrammatic illustration of the planning image processing performed with the apparatus of FIG. 1.

With reference now to FIG. 3, an instrument coordinate circuit 72 determines the position and trajectory of the surgical instrument 36 in instrument space, particularly a coordinate system of the instrument. The instrument coordinate circuit includes a guidance device identification circuit 74 and a mechanical arm assembly position circuit 76. The guidance device identification circuit 74 receives the device identification signal from the one or more guidance devices connected to the mechanical arm and indexes a look up table 78 to retrieve dimensional and functional information. The mechanical arm assembly position circuit 76 is connected with the increment resolvers on the mechanical arm assembly 30 to receive signals indicative of changes of position and orientation of the mechanical arm in instrument space. An instrument-planning scanner correlating processor 80 determines the correlation or transform between the surgical instrument 36 and the volumetric scanner 18 coordinate systems. The correlation or transform is normally described in terms of offset, particularly offset along the axis of the patient support, angular offset or rotation, and scaling. In one embodiment, a calibration instrument is touched to a set of spaced apart markers, preferably eight, which are disposed in a known relationship to the volumetric scanner coordinate system. The markers are preferably in the form of a calibration phantom located in the calibration marker area 16 on the patient support table. By measuring the coordinates of the calibration instrument in the instrument coordinate system while touching each marker, six or more common points in the two coordinate systems are determined. By determining a barrycenter, centroid, or other characteristic point of the common points, the offset between the two coordinate systems is determined. By determining the angular difference between the rays from the barrycenter to each point in each coordinate system, the angular offset is determined. By determining a difference in physical displacement between the barrycenter and the corresponding points in each coordinate system, the scaling factor is determined. Of course, in a system such as the illustrated embodiment in which the instrument and the volumetric scanner are mechanically linked, the transform or relationship between the volumetric scanner and the instrument coordinate system needs only to be calibrated once and, thereafter, is predetermined from the mechanical interconnection between the component parts. The touching of the markers need only be performed once and subsequently used merely to confirm that the instrument and the CT scanner coordinates have not become misaligned between interventional procedures.

Using analogous mathematics or known mechanical relationships as above, an instrument to patient table correlating processor 82 determines the correlation or transform between the patient table and the surgical instrument. Preferably, the calibration phantom described above having the plurality of markers is positioned in a known position on the table to provide a large number of corresponding points in both coordinate systems for the correlating process. Images of the phantom can be utilized to derive transforms between patient table space and planning or real time image coordinate systems.

Table resolvers 84 located in the patient table contribute vertical and longitudinal offsets to the correlation between the surgical instrument and the patient table when the table is raised or lowered and when the patient support 12 is moved axially. An instrument to patient correlation processor 86 determines a correlation between the surgical instrument system and a patient coordinate system. Preferably, this is done by placing the surgical instrument on three or more known reference points on the patient. Such points might include readily identifiable anatomical structures such as the tip of the nose, distinctive points of bones, fiducial markers that are aligned during the volumetric imaging process, or the like.

An instrument to volumetric image coordinate system transform processor 88 receives the correlation or transform from the surgical instrument to planning image processor 80. The instrument to volumetric image processor operates on input position and orientation coordinates in arm space to transform them into volumetric image data space and visa versa. Knowing the position of the surgical instrument in volumetric or planning data space enables the instrument position and orientation to be superimposed on the volumetric planning image data.

During a medical procedure, the patient is positioned in the volumetric planning scanner and a volumetric image is generated. The volumetric image is stored in a volumetric or planning data memory 90. The position of the patient table during the generation of the planning data, particularly as the table moves to generate spiral or slice data, is stored in conjunction with the volumetric planning data such that the data is correlated with the patient table coordinate system. The position of the free end of the arm relative to the patient's body controls the volume planning image data memory or a video processor 92 such that selected slices, projection images, surface renderings, or other conventional displays of the data are generated for display on a planning image display 94. Preferably, the planning image display includes corresponding sagittal coronal axial and oblique slices through a common point of intersection.

Because the planning image display is generated before the surgical procedure, the planning movement of the surgical instrument is preferably displayed in the planning image. The coordinates and trajectory of the surgical instrument are conveyed to the instrument to planning image transform processor 88 for conversion into the planning image coordinate system. The location and trajectory of the instrument in the planning image coordinate system is communicated to the video processor 92 which superimposes the surgical instrument position and trajectory on the CT data display. The position and orientation of the stereotactic arm assembly 30 is communicated to the interventionist control 28, which generates cursor position signals and virtual needle displays which are transformed into the planning image coordinate system 94 and communicated to the video processor 92 to generate a movable cursor point and a virtual needle representation on the planning image display 94. Preferably, the cursor is positioned at the point of intersection of concurrently displayed transverse, coronal, and sagittal views on the volumetric image display 94. As the operator moves the free end of the stereotactic arm assembly through volumetric image data space and as the surgical instrument 36 on the mechanical arm assembly 30 is moved over target areas on the patient, the sagittal, coronal, and transverse views automatically change correspondingly.

Turning once again to FIG. 2, an interchangeable surgical instrument guidance device 100 formed in accordance with a first preferred embodiment of the present invention is shown attached to the free end 40 of the mechanical arm assembly 30. The interchangeable surgical instrument guidance device illustrated is a combined laser and cannula guidance device 102 including an upwardly disposed top end effector member 104 carrying a laser light emitting source 108 and a downwardly disposed bottom end effector member 106 carrying a pair of opposing cannula needle guide elements 110, 112. The opposing needle guide elements are biased together into the position illustrated by a retractable tweezer unit 114 which will be described in greater detail below. The top and bottom end effectors 104, 106 are adapted to each individually provide a distinct identification signal to the instrument coordinate circuit 72 through respective electromechanical connectors 116, 118 which adapt the top and bottom end effectors for connection to the wrist member 62 of the mechanical arm assembly 30.

Figure 4:
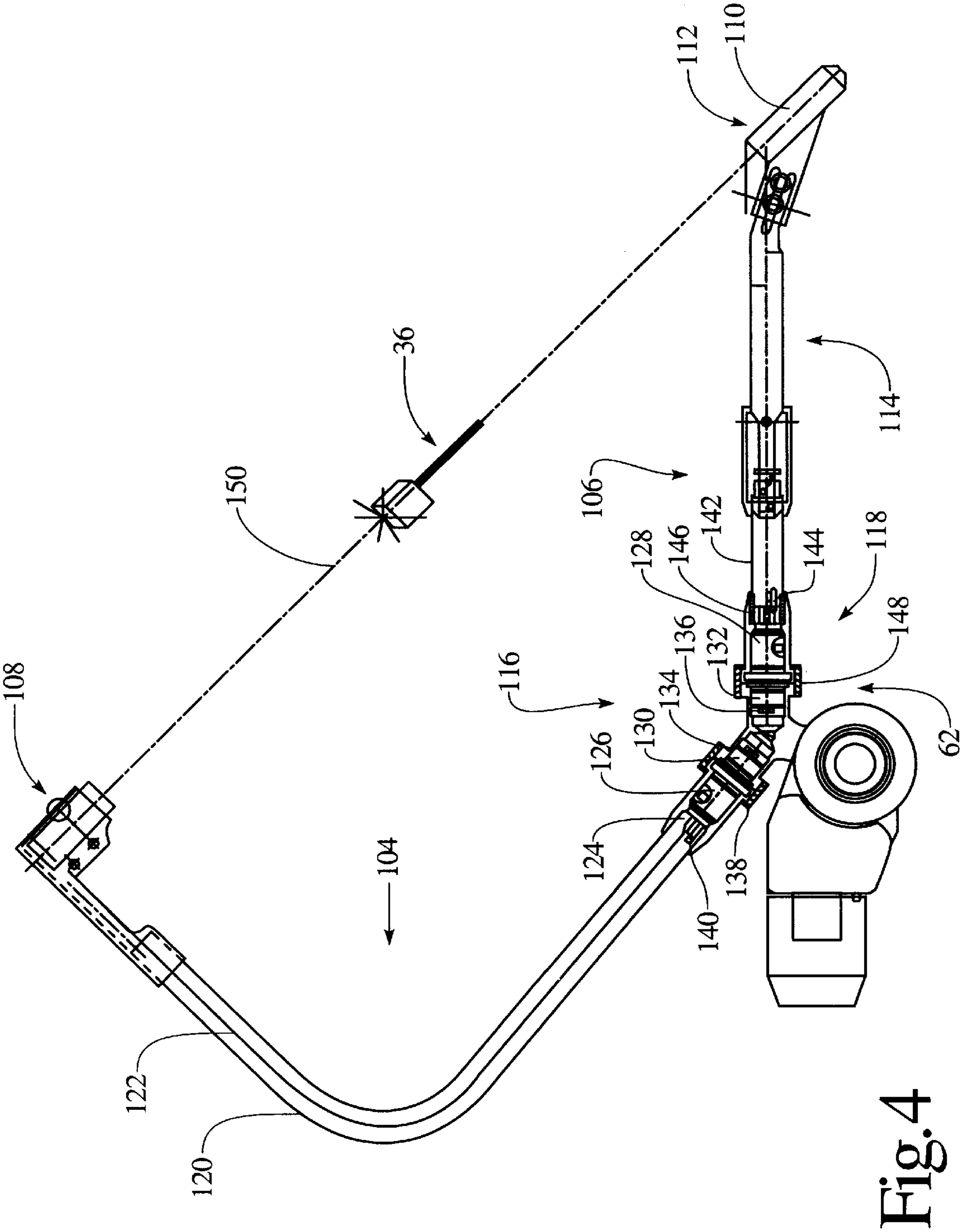
FIG. 4 is a side view in partial cross section of a surgical instrument guidance device formed in accordance with a first preferred embodiment of the present invention.

FIG. 4 illustrates the combined laser and cannula guidance device 102 in greater detail. With reference now to that FIGURE, the top end effector member 104 is formed of a rigid hollow tube member 120 adapted to carry multiple power supply wires 122 within the tube between the laser light source 108 and a first set of electrical pins 124 arranged in an intermateable plug portion 126 of the first electromechanical connector 116. According to the preferred embodiment of the invention, the wrist member 62 includes a pair of first and second intermateable socket portions 130, 132 which carry respective sets of electrical connection pins 134, 136. The first set of electrical connection pins 134 on the wrist member 62 are adapted to electrically and mechanically connect with the first set of electrical pins 124 formed in the intermateable plug portion 126 when the top end effector member 104 is connected to the wrist member. Preferably, an internally threaded nut 138 is provided on the top end effector member 104 for engaging corresponding external threads provided on the wrist member 62.

In addition to the supply of power to the laser light source 108 through the power supply wires 122, the first set of electrical pins 124 are connected to an identification resistor 140 disposed within the rigid hollow tube 120. In accordance with the present invention, the identification resistor 140 provides a unique analog identification value to the instrument coordinate circuit 72 for use as an index into the look up table 78 in a manner described above. Further in accordance with the present invention, each of the interchangeable surgical instrument guidance devices 100 are provided with an identification resistor having an analog resistance value unique to each guidance device. Other equivalent schemes may be used equally to uniquely identify the guide devices such as contact closures, DIP switches, or the like.

With continued reference to FIG. 4, but turning attention next to the bottom end effector member 106, an elongate rigid hollow tube 142 adapts the cannula pair 110, 112 for connection to the wrist member 62. For reasons which will subsequently become apparent, the tube 142 is preferably hollow in order to accommodate lateral retraction of the tweezer unit 114 in a leftward direction as viewed in the FIGURE.

In a manner similar to that described above in connection with the top end effector member, an identification resistor 144, preferably having an analog resistance value unique to the bottom end effector member, is connected to a set of electrical pins 146 provided on the intermateable plug portion 128 of the bottom end effector member. The electrical pins 146 are adapted to engage corresponding intermateable electrical connection pins 136 provided on the intermateable socket portion 132 of the wrist member 62. An internally threaded nut 148 is adapted to engage corresponding external threads formed on the wrist member in a well known manner to securely fasten the bottom end effector member 106 to the wrist member.

Figure 5A:
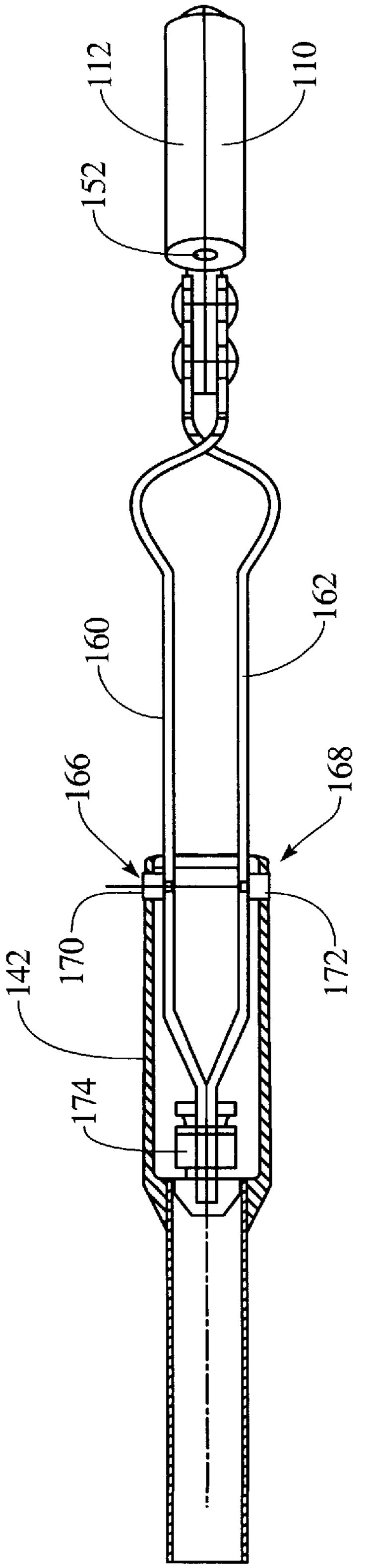
FIGS. 5*a* and 5*b* illustrate respective extended and retracted positions of the lower arm portion of the guidance device shown in FIG. 4.
Figure 5B:
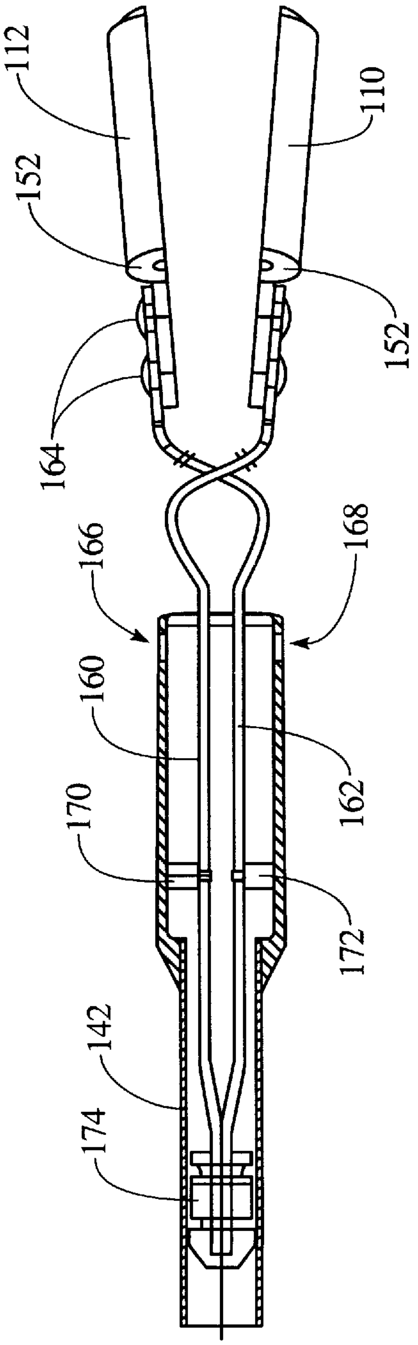

With continued reference to FIG. 4, but with additional references to FIGS. 5*a* and 5*b*, the laser light source 108 is preferably oriented on the top end effector member 104 in a manner to direct a coherent light beam 150 through a needle guide 152 formed on opposing faces of the cannula pair 110, 112. According to well known laser guided surgery techniques, the needle guide 152 and the light beam 150 are oriented on the top and bottom end effector members in precise alignment with each other. In that regard, in order to ensure that the needle guide does not become worn after repeated use during interventional procedures thereby degrading the precision of the surgical guidance device, the cannula pair are preferably disposed after each use. Preferably, the cannula pair members 110, 112 are formed of resilient lexan or polycarbonate and are releasably connected to first and second spring members 160, 162 of the tweezer unit using suitable fasteners such as the set of mushroom-shaped rivets 164 as shown. The rivets are preferably permanently affixed to the first and second spring members 160, 162. According to the preferred embodiment, after each interventional procedure, the used cannula pairs are removed and disposed and, thereafter, a new cannula pair is slid into releasable engagement with the set of rivets 164. Also in accordance with the present invention, the spring constant of the first and second spring members is selected so that the cannula pair are adapted to be separable in the event of unexpected patient movement. Preferably, the spring constant is selected to be both rather stiff to accurately guide surgical instruments and to be somewhat flexible to release the surgical instrument in response to unexpected gross patient movement.

FIG. 5*a* illustrates the retractable tweezer unit 114 in an extended position, and FIG. 5*b* illustrates the tweezer unit in its retracted position. A pair of opposing registration holes 166, 168 are formed in the hollow tube 142 of the bottom end effector member 106 generally as shown. The opposed registration holes are adapted to receive a corresponding pair of locking pins 170, 172 respectively affixed to the first and second spring members 160, 162. The locking pins are easily manually operated against the force of the resiliently biased opposing first and second spring members 160, 162 to dislodge the locking pins out of engagement with the corresponding opposed registration holes 166, 168 formed in the tube 142. As the locking pins are squeezed together, the cannula pair members 110, 112 carried on the first and second spring members 160, 162 separate, releasing a needle or biopsy probe which may be aligned with a target site in the patient. A guide shuttle 174 is adapted to connect the first and second spring members together and to guide the lead edges thereof within the hollow tube 142 as the tweezer unit 114 is retracted into the bottom end effector member 106 to a position shown in FIG. 5*b*.

Figure 6:
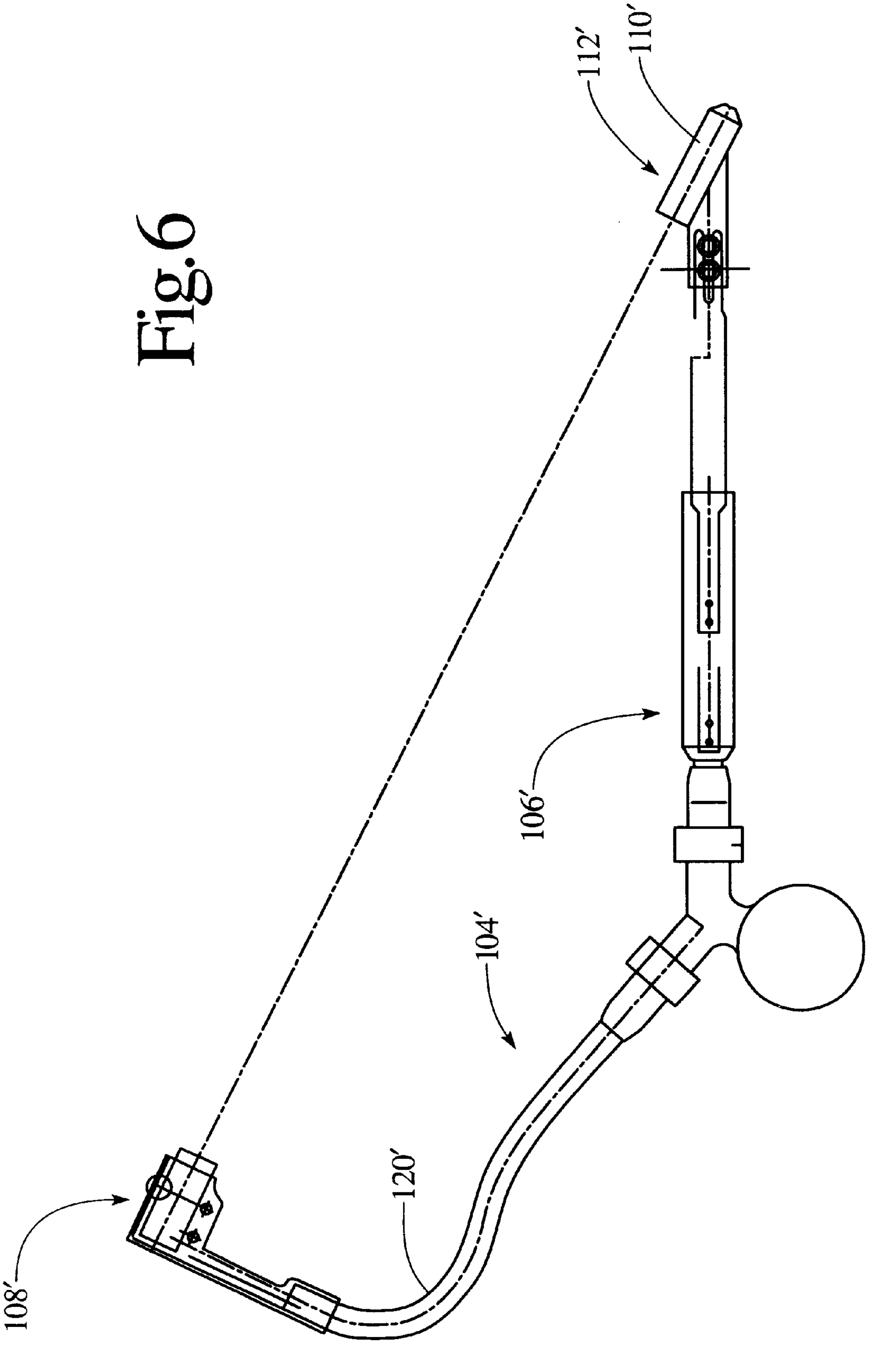
FIG. 6 is a side view of an interchangeable surgical instrument guidance device formed in accordance with a second preferred embodiment of the present invention.

FIG. 6 shows a second preferred embodiment of the laser and cannula guidance device 102' formed in accordance with the present invention to illustrate the interchangeability of the top and bottom end effector members 104', 106' onto the wrist member of an imaging apparatus to accommodate the various needs of a wide range of interventional procedures. In that regard, as illustrated, the top and bottom end effector members 104', 106' are arranged in a substantially different configuration to accommodate large interventional tools between the laser light source 108' and the cannula pair 110', 112'. The top and bottom end effector members 104', 106' carry respective identification resistors (not shown) to communication the physical characteristics of the guidance device to the instrument coordinate circuit 72 in a manner substantially as described above.

Figure 7:
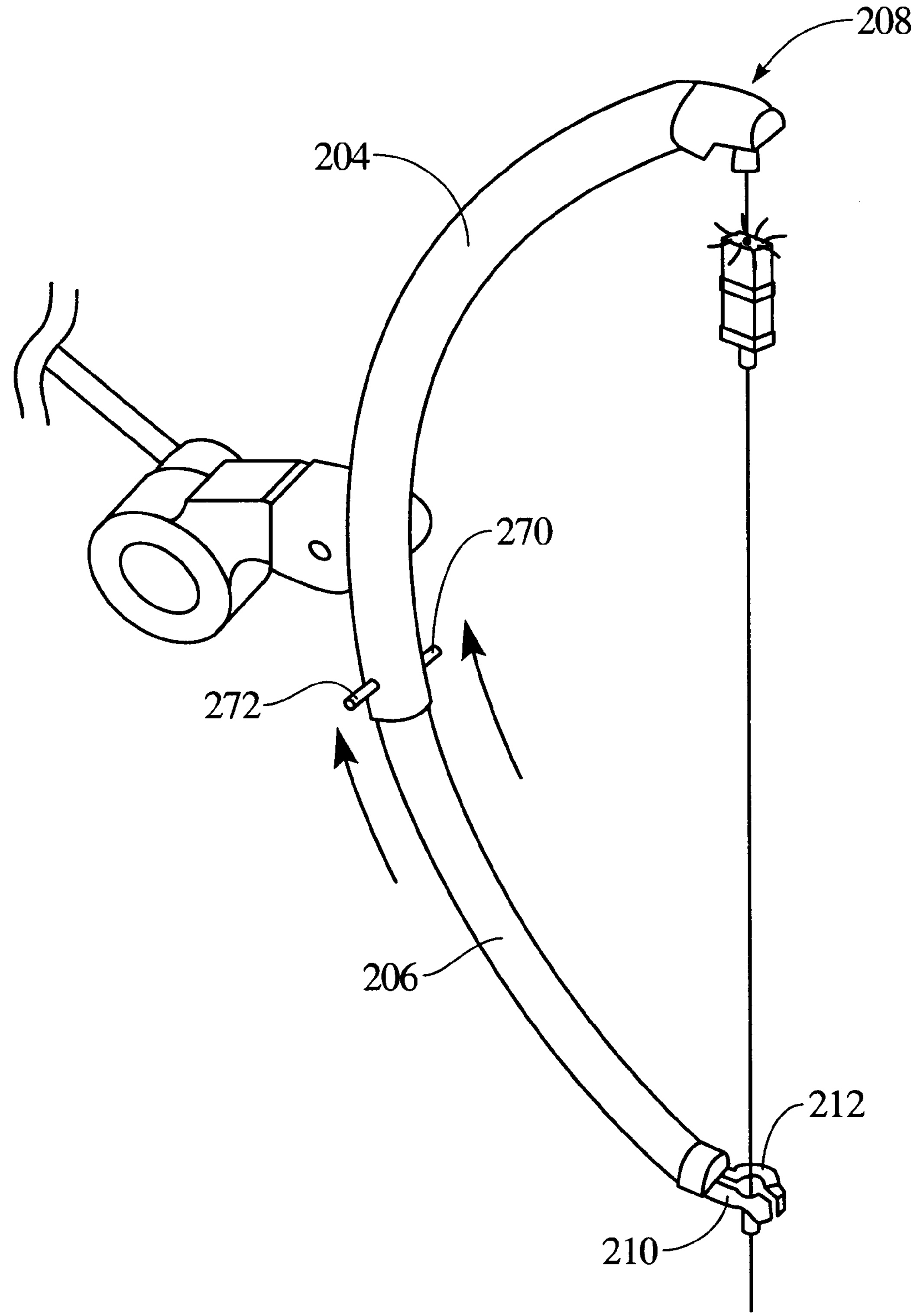
FIG. 7 is a "C" shaped surgical instrument guidance according to an alternative embodiment of the present invention.

FIG. 7 shows yet another alternative embodiment of the combined laser and cannula guidance device of the present invention. The embodiment shown there is adapted for curved co-axial retracting of the lower member into the upper member to provide the instrument with better access to the biopsy field. With reference now to that FIGURE, the top and bottom end effector members 204, 206 are substantially "C" shaped defining an open end between the laser light source 208 carried on the top end effector and the cannula pair 210, 212 carried on the bottom end effector member. According to the alternative preferred embodiment illustrated, the bottom end effector member 206 is telescopically retractable into the top end effector member 204 along an arcuate path substantially following the "C" shaped configuration of the guidance device 202. Any suitable arrangements of mechanical locking mechanisms and slide devices may be used to lock the bottom end effector member into the position illustrated and to facilitate smooth retraction into the top effector member respectively. However, preferably, locking pins 270, 272 and guide shuttles are used substantially in a manner described above.

Figure 8:
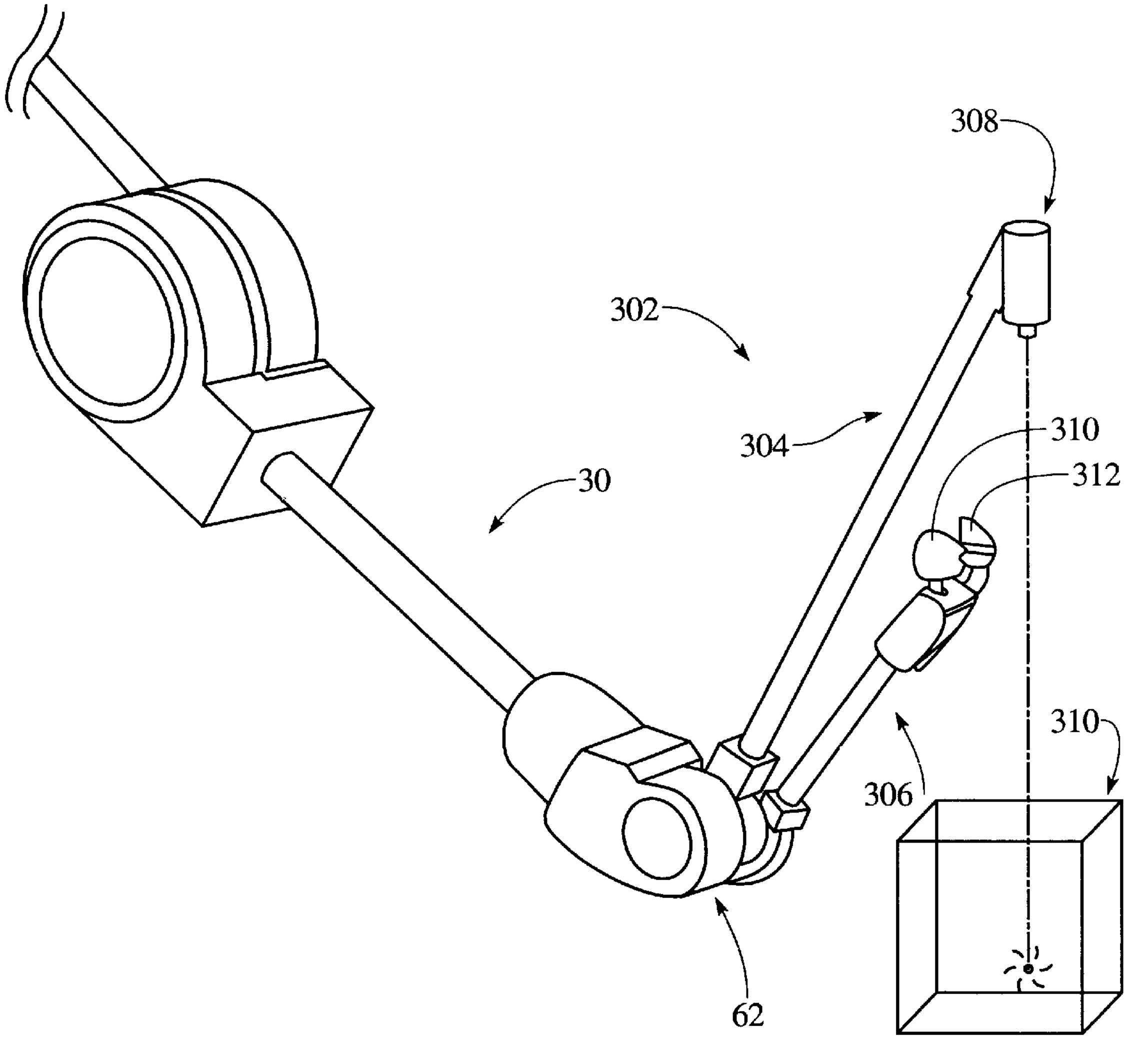
FIG. 8 is a perspective view of an interchangeable surgical instrument guidance device according to yet another alternative embodiment of the present invention.

With reference next to FIG. 8, yet another alternative embodiment of the subject invention is illustrated. With reference now to that FIGURE, a combined laser and cannula guidance device 302 includes top and bottom end effector members 304, 306 which are separately rotatable on the wrist member 62 of the mechanical arm assembly 30. The top end effector member 304 carries the laser light source 308 and the bottom end effector member 306 carries a cannula pair 310, 312. The bottom end effector member 306 is selectively rotatably removable from the biopsy field 310 shown in phantom as an alternative to the linear retraction of the tweezer unit 114 described above. Suitable locking pin members and other mechanical registration devices may be used to permit selective extended (rotated downwardly) and retracted (rotated upwardly) positions of the bottom end effector member 306.

Figure 9:
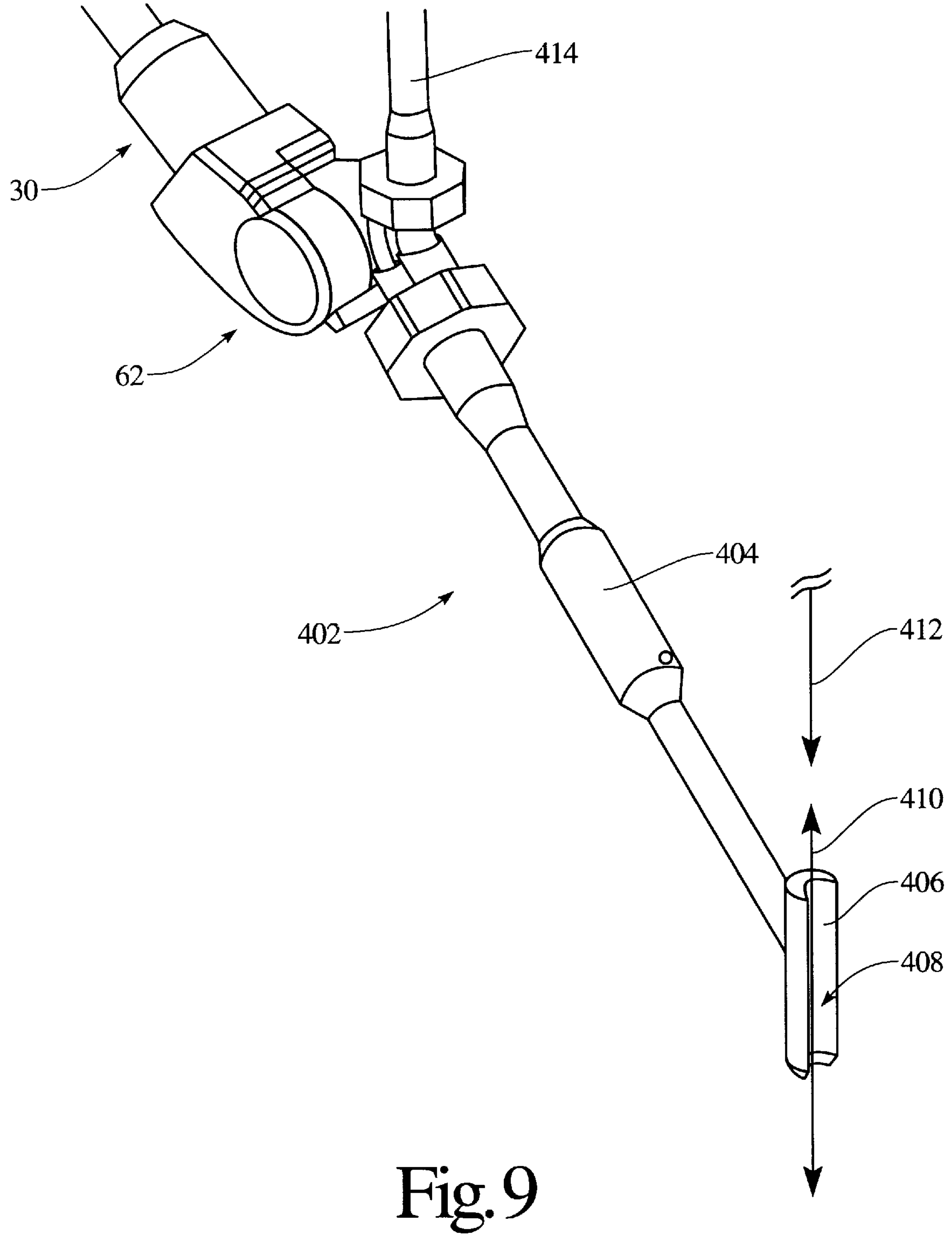
FIG. 9 is a perspective view of an interchangeable surgical instrument guidance device according to yet another alternative embodiment of the present invention.

With reference lastly to FIG. 9, yet another alternative embodiment of the subject invention is illustrated. With reference now to that FIGURE, a V-groove needle guide device 402 is adapted to engage the wrist member 52 of the mechanical arm assembly 30. The needle guide includes an elongate extension member 404 which includes, on a free end thereof, a guide cannula 406. The guide cannula is substantially cylindrical in shape and includes a V-groove formed therein. The V-groove defines a needle guide trajectory 410, useful by interventionists to guide biopsy probes, catheters or other elongate surgical instruments. In the alternative preferred embodiment illustrated, the trajectory 410 of the V-groove needle guide is adapted to co-axially register with a laser light beam guide 412 generated by a laser light source (not shown) supported from overhead by an upper end effector member 414. The laser light source is supported on the upper end effector member 414 in a manner substantially as described above.

The invention has been described with reference to the preferred embodiment. Obviously, modifications and alterations will occur to others upon a reading and understanding of this specification. It is intended to include all such modifications and alterations insofar as they come within the scope of the appended claims or the equivalents thereof.

Having thus described the invention, it is claimed:

1. A stereotactic guide apparatus for use with a CT scanner device in guiding the entry of a surgical instrument associated with the guide apparatus into a patient's body during a laser guided interventional procedure, the guide apparatus comprising:

a stereotactic arm member having a first base end rigidly connected to the CT scanner device and a second free end movable relative to the CT scanner device;

a first end effector member on the free end of the stereotactic arm member, the first end effector member including a guide channel defining an insertion path, the guide channel permitting relative motion between the stereotactic guide apparatus and the associated surgical instrument along said insertion path; and, a second end effector member on the free end of the stereotactic arm member, the second end effector member including a laser light source generating a laser light guide beam co-axially aligned with said insertion path.

2. The stereotactic guide apparatus according to claim 1 wherein each of the first and second end effector members are selectively releasably attached to said second free end of the stereotactic arm member.

3. The stereotactic guide apparatus according to claim 2 wherein:

the first end effector member is adapted to provide a first device identification signal to the CT scanner device through the stereotactic arm member; and, the second end effector member is adapted to provide a second device identification signal to the CT scanner device through the stereotactic arm member.

4. The stereotactic guide apparatus according to claim 3 further comprising:

a first electromechanical coupler for connecting the first end effector member to the stereotactic arm member; and, a second electro-mechanical coupler for connecting the second end effector to the stereotactic arm member.

5. The stereotactic guide apparatus according to claim 4 wherein:

the first electromechanical coupler is adapted to connect a third end effector having a second guide channel to the free end of the stereotactic arm member; and, the second electromechanical coupler is adapted to connect a fourth end effector having a second laser light source to the free end of the stereotactic arm member.

6. The stereotactic guide apparatus according to claim 5 wherein:

the third end effector is connected to the free end of the stereotactic arm member and is adapted to provide a third devise identification signal to the CT scanner device through the stereotactic arm member; and, the fourth end effector is connected to the free end of the stereotactic arm member and is adapted to provide a fourth device identification signal to the CT scanner device through the stereotactic arm member.

7. The stereotactic guide apparatus according to claim 1 wherein each of the first and second end effector members are selectively pivotally attached to the free end of the stereotactic arm member.

8. The stereotactic guide apparatus according to claim 7 wherein each of the first and second end effector members are independently pivotally attached to the free end of the stereotactic arm member so that the second end effector can be pivoted upwardly and away from the insertion path to facilitate the entry of the associated surgical instrument into the patient's body.

9. The stereotactic guide apparatus according to claim 1 wherein said guide channel is retractable relative to the insertion path and into the first end effector to facilitate the entry of the associated surgical instrument into the patient's body.

10. The stereotactic guide apparatus according to claim 9 wherein said guide channel is retractable relative to the insertion path following a substantially arcuate path.

11. The stereotactic guide apparatus according to claim 9 wherein said guide channel is retractable relative to the insertion path following a substantially linear path.

12. The stereotactic guide apparatus according to claim 9 wherein the guide channel is formed between a pair of opposing tweezer fingers biased in a normally closed orientation.

13. The stereotactic guide apparatus according to claim 3 wherein:

the first end effector member carries a first identification resistor to generate said first device identification signal, the first device identification signal being indicative of physical characteristics of the first end effector member; and, the second end effector member carries a second identification resistor to generate said second device identification signal, the second device identification signal being indicative of physical characteristics of the second end effector member.

14. The stereotactic guide apparatus according to claim 1 wherein the guide channel is formed between a pair of opposing tweezer fingers biased in a normally closed orientation.

15. The stereotactic guide apparatus according to claim 1 wherein the guide channel comprises a needle guide defined between opposing faces of a cannula pair.

16. The stereotactic guide apparatus according to claim 1 wherein the guide channel includes a V-groove formed on the first end effector member.

17. A guidance device for use with a stereotactic imaging system having an arm member with a first base end rigidly connected to a CT scanner device and a second free end movable relative to the CT scanner device, the guidance device for guiding the entry of a surgical instrument associated with the guidance device along an insertion path into a patient's body during a stereotactic interventional procedure, the guidance device comprising:

a guide channel member on the free end of the stereotactic arm member defining a surgical instrument insertion path, the guide channel member permitting relative motion between the guidance device and the associated surgical instrument along said insertion path; and, a laser light source on the free end of the stereotactic arm member, the laser light source being adapted to generate a laser light guide beam co-axially aligned with said surgical instrument insertion path.

18. The guidance device according to claim 17 wherein:

each of the guide channel member and the laser light source are selectively releasably attached to said free end of the stereotactic arm member;

the guide channel member is adapted to provide a first device identification signal to the CT scanner device through the stereotactic arm member, the first device identification signal being indicative of physical characteristic of the guide channel member; and, the laser light source is adapted to provide a second device identification signal to the CT scanner device through the stereotactic arm member, the second device identification signal being indicative of physical characteristic of the laser light source.

19. The guidance device according to claim 17 wherein each of the guide channel member and the laser light source are independently pivotally attached to the free end of the stereotactic arm member so that the laser light source can be pivoted upwardly and away from the insertion path to facilitate the entry of the associated surgical instrument into the patient's body.

20. The guidance device according to claim 17 wherein the guide channel member is formed as a one of:

a pair of opposing tweezer fingers biased in a normally closed orientation;

a needle guide defined between opposing faces of a cannula pair; and, a V-groove formed on the free end of the stereotactic arm member.

* * * * *